United States Patent [19]

Bouchara

[11] 3,957,850

[45] May 18, 1976

[54] PHENYLACETIC ACID DERIVATIVES
[76] Inventor: Emile Bouchara, 75 bis, Avenue Foch, 75 Paris, France
[22] Filed: May 9, 1972
[21] Appl. No.: 251,680

[30] Foreign Application Priority Data
  May 17, 1971  France .............................. 71.17714

[52] U.S. Cl. ...................... 260/471 R; 260/518 R; 424/309; 424/319
[51] Int. Cl.² ....................................... C07F 101/44
[58] Field of Search ..................... 260/518 R, 471 R

[56] References Cited
UNITED STATES PATENTS

| | | | |
|---|---|---|---|
| 3,669,956 | 6/1972 | Borck et al. .................... | 260/293.81 |
| 3,673,212 | 6/1972 | Denss et al. .................... | 260/326.41 |
| 3,673,243 | 6/1972 | Yamamoto et al. ............ | 260/518 R |
| 3,697,590 | 10/1972 | Boissier et al.................... | 260/518 R |

OTHER PUBLICATIONS

Finar, I. L., *Organic Chemistry*, (Vol. I), (1963) pub. by Richard Clay & Co. Ltd. pp. 282, 303 & 312.

Carney, R., et al. *Chemical Abstracts*, Vol. 72, (1970) p. 55024c.

*Primary Examiner*—Richard L. Raymond
*Attorney, Agent, or Firm*—Young & Thompson

[57] ABSTRACT

The present invention relates to phenylacetic acid derivatives having the general formula:

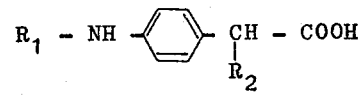

in which $R_1$ represents a lower alkyl radical, a lower alkenyl radical, a lower alkynyl radical or an aryl(-lower) alkyl radical, $R_2$ represents hydrogen or a methyl radical, their esters and their salts with bases and acids.

Said derivatives have in particular an analgesic and/or anti-inflammatory activity.

19 Claims, No Drawings

PHENYLACETIC ACID DERIVATIVES

This invention relates to new phenylacetic acid derivatives, to a process for their preparation and to their therapeutic applications.

The present invention relates to new phenylacetic acid derivatives having the general formula:

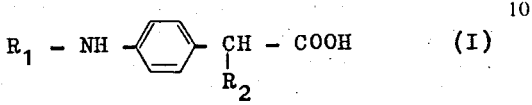

in which $R_1$ represents a lower alkyl radical, a lower alkenyl radical, a lower alkynyl radical or an aryl (lower) alkyl radical, $R_2$ represents hydrogen or a methyl radical, their esters and their salts with bases and acids.

The term "lower" which is used in the preceding definition means that said radicals contain up to 6 carbon atoms.

The derivatives according to the present invention in which $R_2$ is a methyl radical possess an asymmetrical carbon atom. The present invention includes within its scope both the enanthiomorphic isomers and the racemates of said derivatives.

The derivatives according to the present invention may be prepared by alkylation of an amino-acid having the formula:

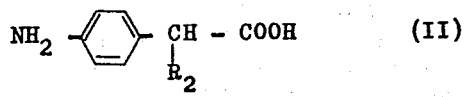

with an alkyl halide having the formula $R_1X$, within a suitable solvent, in the presence of an acid acceptor, $R_1$ and $R_2$ having the aforementioned meaning and X representing a halogen atom.

Useful solvents include particularly alcohols such as ethanol and isopropanol.

Useful acid acceptors include particularly potassium carbonate or pyridine.

The reagents are advantageously used in substantially stoichiometric amounts, and reaction time may be vary within a range from a few minutes to several hours, as the case may be.

In addition to a major amount of the monoalkylated derivative, the resulting reaction product contains small amounts of the dialkylated derivative and of the starting amino-acid. The derivatives according to the invention may be separated according to conventional techniques such as by fractional crystallization, fractional distillation in vacuo or column chromatography.

The amino-acid of the formula (II) is advantageously used in the form of an ester, particularly of a lower alkyl ester. The acid of the formula (I) may then be obtained by hydrolysis of the resulting ester, in basic medium.

The present invention relates also to a novel process for the preparation of amino-acid of the formula (II) in which $R_2$ is a methyl radidal and of its esters. The process comprises reducing 2-(p-nitrophenyl)acrylic acid prepared according to J. H. Schauble and E. Hertz, J.Org.Chem., 35, p. 2529, 1970, and its esters, respectively, by catalytic hydrogenation.

The compounds according to the present invention possess analgesic and/or anti-inflammatory properties. Said compounds, and particularly:
p-ethylaminophenylacetic acid
p-n-propylaminophenylacetic acid
p-n-butylaminophenylacetic acid
p-isopropylaminophenylacetic acid
p-benzylaminophenylacetic acid
p-allylaminophenylacetic acid
p-methallylaminophenylacetic acid
p-propargylaminophenylacetic acid
2-(p-methylaminophenyl)-propionic acid
2-(p-ethylaminophenyl)-propionic acid
2-(p-n-propylaminophenyl)-propionic acid
2-(p-n-butylaminophenyl)-propionic acid
2-(p-isopropylaminophenyl)-propionic acid
2-(p-benzylaminophenyl)-propionic acid
2-(p-allylaminophenyl)-propionic acid
2-(p-methallylaminophenyl)-propionic acid
2-(p-propargylaminophenyl)-propionic acid, and
their therapeutically acceptable esters and salts may be used for the treatment of muscular, articular or nervous algias, of rheumatic conditions, dental pains, zona, migraines and as complementary treatment in feverish or infectious conditions. They may be administered by the oral, transcutaneous or rectal route, or they may be applied topically onto the skin and mucous membranes.

The compounds may be formulated as injectable solutions or suspensions filled in ampoules, in multiple-dose vials, as tablets, coated tablets, capsules, syrups, suppositories and ointments.

The useful daily dosage regimen for said compounds is comprised within a range from 100 mg to 2 g daily, according to the route of administration. Their pharmaceutical formulations such as injectable solutions or suspensions, tablets, coated tablets, syrups, suppositories and ointments are prepared according to the usual procedures.

Each unit dose for oral, transcutaneous or rectal administration may contain from 50 mg to 500 mg of active ingredient.

The following examples illustrate the invention.

EXAMPLE 1

Ethyl para-allylaminophenylacetate

A mixture of ethyl p-aminophenylacetate (36 g), allyl bromide (24.2 g), potassium carbonate (28 g) and isopropanol (300 ml) is boiled during 16 hours.

The reaction mixture is then filtered and evaporated to dryness, in vacuo. Isolation by chromatographic separation over silica gives 12 g of ethyl p-allylaminophenylacetate as a slightly yellow oil.

Analysis: for $C_{13}H_{17}NO_2 = 219.28$ Calculated: C% 71.20; H% 7.81; N% 6.39; Found: C% 71.21, H% 7.87; N% 6.42.

EXAMPLE 2 p-Allylaminophenylacetic acid

A mixture of ethyl p-allylaminophenylacetate (9 g) in normal sodium hydroxide (200 ml) and methanol (200 ml) is left aside at room temperature during 16 hours. After neutralization with 1N hydrochloric acid (200 ml), it is concentrated to dryness in vacuo.

Extraction of the residue with ether gives an oil which solidifies rapidly. Recrystallization from isopropyl ether gives p-allylaminophenylacetic acid (6.2 g) as colorless prisms. M.p. (instantaneous)= 86°–87°C.

Analysis: for $C_{11}H_{13}NO_2$ = 191.22 Calculated: C% 69.09; H% 6.85; N% 7.33; Found: C% 68.98; H% 6.82; N% 7.34.

EXAMPLE 3 p-Ethylaminophenylacetic acid

Ethyl p-aminophenylacetate (5.4 g), ethyl iodide (4.7 g), pyridine (2.4 g) and isopropanol (50 ml) are boiled together during 6 hours. The reaction mixture is concentrated in vacuo, taken up into water, extracted with ether and dried, and the solvent is then removed. Ethyl p-ethylaminophenylacetate (2 g) is isolated by chromatography over silica. Saponification in the cold, in methanolic sodium hydroxide, gives 1.2 g of p-ethylaminophenylacetic acid. M.p. inst. = 123°C after recrystallization from ethyl acetate.

Analysis: for $C_{10}H_{13}NO_2$ = 179.22 Calculated: C% 67.01; H% 7.31; N% 7.82; Found: C% 66.92; H% 7.34; N% 7.87.

EXAMPLE 4 a. Methyl 2-(p-aminophenyl)propionate

Methyl 2-(p-nitrophenyl)acrylate (52 g) is hydrogenated in ethanol (500 ml) in the presence of 5% palladium-over-charcoal, while maintaining the temperature at +5°C. The theoretical amount of hydrogen is taken up within one hour.

After separation of the catalyst and concentration to dryness, the resulting material gives methyl 2-(p-aminophenyl)proprionate which crystallizes: M.p. (inst.) = 40°–43°C.

Analysis: for $C_{10}H_{13}NO_2$ = 179.21 Calculated: C% 67.01; H% 7.30; N% 7.81; Found: C% 66.86; H% 7.20; N% 7.77.

b. Methyl 2-(p-allylaminophenyl)-propionate

A mixture of methyl 2-(p-aminophenyl)-propionate (40 g), allyl bromide (27 g), and potassium carbonate (15.4 g) in isopropanol (450 ml) is boiled during 16 hours.

The reaction mixture is then filtered and concentrated to dryness in vacuo. Chromatographic separation over silica gives methyl 2-(p-allylaminophenyl)-propionate, as a slightly yellow oil.

Analysis: for $C_{13}H_{17}NO_2$ = 219.28 Calculated: C% 71.20; H% 7.81; N% 6.39; Found: C% 70.88; H% 7.99; N% 6.74.

EXAMPLE 5

2-(p-Isopropylaminophenyl)-propionic acid

A mixture of 2-(p-aminophenyl)propionate (5.4 g), isopropyl bromide (5g), pyridine (5 ml) and ethanol (80 ml) is boiled during 16 hours. The reaction mixture is concentrated in vacuo, taken up into water, extracted with ether, dried, after which the solvent is removed. Chromatography over silica gives 2.2 g of methyl 2-(p-isopropylaminophenyl)propionate.

Saponification in the cold in methanolic sodium hydroxide gives 1.8 g 2-(p-isopropylaminophenyl)propionic acid. M.p. inst.= 115°–116°C after recrystallization from isopropyl ether.

Analysis: for $C_{12}H_{17}NO_2$ = 207.27 Calculated: C% 69.53; H% 8.27; N% 6.76; Found: C% 69.56; H% 8.22; N% 6.87.

EXAMPLE 6

2-(p-Allylaminophenyl)-propionic acid

A mixture of methyl 2-(p-allylaminophenyl)propionate (13.4 g), normal sodium hydroxide (100 ml) and methanol (200 ml) is left aside at room temperature during 24 hours and is then neutralized with normal hydrochloric acid (100 ml). The methanol is removed in vacuo, in the cold, and the aqueous solution is extracted with ether, to give a white solid.

Recrystallization from hexane gives 2-(p-allylaminophenyl)-propionic acid (8 g) as colorless prisms. M.p. inst. = 67°C.

Analysis: for $C_{12}H_{15}NO_2$ = 205.25 Calculated: C% 70.21; H% 7.37; N% 6.82; Found: C% 70.22; H% 7.41; N% 6.83.

EXAMPLE 7

Methyl 2-(p-methallylaminophenyl)-propionate hydrochloride

A mixture of methyl 2-(p-aminophenyl)-propionate (44.75 g), methallyl chloride (34 g) and pyridine (30 ml) in isopropanol (400 ml) is boiled during 30 hours. The solvent is removed in vacuo and the residue is taken up into water and ether. After separation, the organic phase is washed repeatedly with water, after which it is dried and concentrated in vacuo. The resulting oil is fractionally distilled in vacuo (0.1 mm Hg).

5 g of oil essentially consisting of methyl 2-(p-aminophenyl)propionate are collected at 115°–120°C.

30 g of oil consisting of a mixture of mono- (80%) and disubstituted (20%) amines is collected at 128°–130°C. This oil is used to prepare the hydrochloride which is recrystallized from ethyl acetate, to give white crystals (22.7 g) melting at 115°C (inst.). Hydrochloride of the pure mono-alkylated derivative:

Analysis: for $C_{14}N_{20}ClNO_2$ = 269.76 Calculated: C% 62.33; H% 7.47; N% 5.20; Cl% 13.14; Found: C% 61.99; H% 7.21; N% 5.26; Cl% 13.30.

EXAMPLE 8

2-(p-Allylaminophenyl)propionic acid, lithium salt 2-(p-Allylaminophenyl)-propionic acid (4.11 g) is dissolved in 1N lithia (20 ml). The water is removed in vacuo at a temperature not in excess of 30°C, to give a solid which is taken up into ether. After repeatedly washing with this solvent, pink crystals (3.2 g) melting at 220°C (inst.) are isolated.

Analysis: for $C_{12}H_{14}LiNO_2$ = 211.18 Calculated: C% 68.24; H% 6.68; N% 6.63; Li% 3.29; Found: C% 68.09; H% 6.57; N% 6.65; Li% 3.42.

EXAMPLE 9 p-n-Propylaminophenylacetic acid

The procedure of Example 3 is used. Beige crystals are obtained. M.p. (inst.)= 113°C.

Analysis: for $C_{11}H_{15}NO_2$ = 193.24 Calculated: C% 68.37; H% 7.82; N% 7.25; Found: C% 68.28; H% 7.88; N% 7.13.

EXAMPLE 10 p-n-Butylaminophenylacetic acid

The procedure of Example 3 is used. Cream-colored crystals are obtained. M.p. (inst.) = 102°C.

Analysis: for $C_{12}H_{17}NO_2$ = 207.27 Calculated: C% 69.53; H% 8.27; N% 6.76; Found: C% 69.62; H% 8.33; N% 6.79.

EXAMPLE 11 p-Isopropylaminophenylacetic acid

The procedure of Example 3 is used, to give cream-colored crystals, M.p. (inst.) = 148°C.

Analysis: for $C_{11}H_{15}NO_2$ = 193.25 Calculated: C% 68.36; H% 7.82; N% 7.25; Found: C% 68.11; H% 7.68; N% 7.23.

EXAMPLE 12 p-Benzylaminophenylacetic acid

The procedure of Example 3 is used, to give white crystals. M.p. (inst) = 123°C.

Analysis: for $C_{15}H_{15}NO_2$ = 241.28 Calculated: C% 74.66; H% 6.26; N% 5.80; Found: C% 74.75; H% 6.32; N% 5.83.

EXAMPLE 13 p-Methallylaminophenylacetic acid

The procedure of Example 3 is used, to give white crystals, M.p. (inst.) = 120°C.

EXAMPLE 14

Ethyl p-methallylaminophenylacetate

The procedure of Example 3 is used, omitting the saponification step, to give an oil: b.p. = 140°C /0.1 mm Hg.

EXAMPLE 15 p-Propargylaminophenylacetic acid

The procedure of Example 3 is used, to give white crystals, M.p. (inst.) = 100°C.

Analysis: for $C_{11}H_{11}NO_2$ = 189.21 Calculated: C% 69.82; H% 5.86; N% 7.41; Found: C% 69.80; H% 5.73; N% 7.60.

EXAMPLE 16

2-(p-Methylaminophenyl)propionic acid

The procedure of Example 5 is used, to give white crystals, M.p. (inst.) = 117°–118°C.

Analysis: for $C_{10}H_{13}NO_2$ = 179.20 Calculated: C% 67.01; H% 7.31; N% 7.82; Found: C% 67.14; H% 7.29; N% 7.87.

EXAMPLE 17

2-(p-Ethylaminophenyl)propionic acid

The procedure of Example 5 is used, to give white crystals. M.p. (inst.) = 102°–103°C Analysis: for $C_{11}H_{15}NO_2$ = 193.25 Calculated: C% 68.37; H% 7.82; N% 7.25; Found: C% 68.49; H% 7.89; N% 7.08.

EXAMPLE 18

2-(p-n-Propylaminophenyl)propionic acid

The procedure of Example 5 is used, to give white crystals. M.p. (inst.) = 87°C.

Analysis: for $C_{12}H_{17}NO_2$ = 207.27 Calculated: C% 69.53; H% 8.27; N% 6.76; Found: C% 69.48; H% 8.26; N% 6.80.

EXAMPLE 19

2-(p-n-Butylaminophenyl)propionic acid

The procedure of Example 5 is used, to give white crystals. M.p. (inst.) = 109°C.

Analysis: for $C_{13}H_{19}NO_2$ = 221.29 Calculated: C% 70.55; H% 8.65; N% 6.33; Found: C% 70.43; H% 8.84; N% 6.30.

EXAMPLE 20

2-(p-Benzylaminophenyl)acid

The procedure of Example 5 is used, to give white crystals. M.p. (inst.) = 125°C.

EXAMPLE 21

2-(p-Methallylaminophenyl)propionic acid

The procedure of Example 5 is used, to give cream-colored crystals. M.p. (inst.) = 107°C.

Analysis: for $C_{13}H_{17}NO_2$ = 219.27 Calculated: C% 71.20; H% 7.81; N% 6.39; Found: C% 70.87; H% 7.80; N% 6.42.

EXAMPLE 22

2-(p-Propargylaminophenyl)-propionic acid

The procedure of Example 5 is used, to give cream-colored crystals. M.p. (inst.) = 90°C.

Analysis for $C_{12}H_{13}NO_2$ = 203.23 Calculated: C% 70.92; H% 6.45; N% 6.89; Found: C% 70.93; H% 6.44; N% 6.99.

EXAMPLE 23

2-(p-Allylaminophenyl)propionic acid, sodium salt

The procedure of Example 8 is used, to give beige-colored crystals. M.p. (inst.) = 50°C.

The results of toxicological and pharmacological tests reported below demonstrate the highly interesting properties of the compounds according to the invention.

1. Acute toxicity determination

Acute toxicity tests were carried out with lots of 10 female mice of "Swiss" strain, weighing from 19 to 21 g.

The means lethal dose ($LD_{50}$) by the oral route was determined by means of the method of BEHRENS and KARBER after keeping the animals under observation during 48 hours. The resulting data are tabulated in Table 1. In this table are also set forth the $LD_{50}$ of acetylsalicylic acid and of indometacine used as reference materials.

2. Pharmacological properties a. Study of the analgesic activity

The analgesic activity was determined by the inhibition test of the peritoneal pain induced by injection of acetic acid.

This test is based on the finding by KOSTER and co-workers (Feder. Proceed., 1959, 18, 412) according to which intraperitoneal injection of 0.2 ml/20 g of a 6°/oo acetic acid solution induces writhing and stretching movements in mice. The materials having an analgesic action reduce or eliminate this syndrome.

Lots of 10 mice are given orally the various test compounds, 30 minutes prior to injection of the challenging material. The writhing movements are counted during 15 minutes and the analgesic effect is expressed as percent decrease of the number of stretching movements with respect to the reference animals.

The same test was carried out with acetylsalicylic acid. The various results obtained are summarized in Table 2.

b. Study of the anti-inflammatory activity

The anti-inflammatory activity was determined by means of the test of the carragheenin-induced edema of the pawsin rats.

Male rats weighing about 120 g are administered 0.1 ml of an 0.5% carragheenin suspension (plantar subaponeurotic injection) one hour after oral treatment with the various test compounds.

The volume of the rear paws is measured prior to injection of the inflammatory agent, and then 2, 3 and 4 hours after injection.

The difference between the volume of the paws of the treated animals and the volume of the paws of the reference animals evidences the anti-inflammatory action of the various test compounds.

The same test was carried out with indometacine. The resulting data are tabulated in following Table 3.

Table 1

ACUTE TOXICITY (Mice)

| | $LD_{50}$ mg/kg oral route |
|---|---|
| p-allylaminophenylacetic acid | 1550 |
| ethyl p-allylaminophenylacetate | 2400 |
| p-ethylaminophenylacetic acid | 2910 |
| p-n-propylaminophenylacetic acid | 2400 |
| p-n-butylaminophenylacetic acid | 1200 |
| p-isopropylaminophenylacetic acid | 2400 |
| p-benzylaminophenylacetic acid | 2400 |
| p-propargylaminophenylacetic acid | 2910 |
| 2-(p-allylaminophenyl)propionic acid | 1780 |
| methyl 2-(p-allylaminophenyl)propionate | 1600 |
| 2-(p-methylaminophenyl)propionic acid | >3200 |
| 2-(p-ethylaminophenyl)propionic acid | 2400 |
| 2-(p-n-propylaminophenyl)-propionic acid | 2400 |
| 2-(p-n-butylaminophenyl)propionic acid | 1200 |
| 2-(p-isopropylaminophenyl)propinoic acid | 2400 |
| 2-(p-benzylaminophenyl)propionic acid | 880 |
| 2-(p-methallylaminophenyl)propionic acid | 2400 |
| 2-(p-propargylaminophenyl)propionic acid | 2400 |
| methyl 2-(p-methallylaminophenyl)-propionate hydrochloride | 2400 |
| ethyl p-methallylaminophenylacetate | 2400 |
| p-methallylaminophenylacetic acid | 1780 |
| 2-(p-allylaminophenyl)propionic acid, lithium salt | 2910 |
| indometacine | 50 |
| acetylsalicylic acid | 1500 |

Table 2

ANALGESIC ACTIVITY

| | Oral doses mg/kg | % analgesia |
|---|---|---|
| p-allylaminophenylacetic acid | 100 | 51 |
| ethyl p-allylaminophenylacetate | 67 | 41 |
| p-ethylaminophenylacetic acid | 16 | 37.5 |
| p-n-propylaminophenylacetic acid | 27 | 49 |
| p-n-butylaminophenylacetic acid | 33 | 51 |
| p-isopropylaminophenylacetic acid | 13.5 | 42 |
| p-benzylaminophenylacetic acid | 67 | 33 |
| p-propargylaminophenylacetic acid | 36 | 51 |
| 2-(p-allylaminophenyl)propionic acid | 20 | 50 |
| methyl 2-(p-allylaminophenyl)propionate | 25 | 57 |
| 2-(p-methylaminophenyl)propionic acid | 36 | 60 |
| 2-(p-ethylaminophenyl)propionic acid | 27 | 44 |
| 2-(p-n-propylaminophenyl)-propionic acid | 13.5 | 61 |
| 2-(p-n-butylaminophenyl)propionic acid | 13 | 50 |
| 2-(p-isopropylaminophenyl)propionic acid | 27 | 56 |
| 2-(p-benzylaminophenyl)propionic acid | 10 | 47 |
| 2-(p-methallylaminophenyl)propionic acid | 7 | 58 |
| 2-(p-propargylaminophenyl)propionic acid | 13.5 | 55 |
| methyl 2-(p-methallylaminophenyl)-propionate hydrochloride | 27 | 49 |
| ethyl p-methallylaminophenylacetate | 67 | 51 |
| p-methallylaminophenylacetic acid | 49 | 32 |
| 2-(p-allylaminophenyl)propionic acid, | 81 | 28 |

Table 2-continued

ANALGESIC ACTIVITY

| | Oral doses mg/kg | % analgesia |
|---|---|---|
| lithium salt acetylsalicylic acid | 100 | 55 |

Table 3

ANTI-INFLAMMATORY ACTIVITY

| | Oral doses* mg/kg | % inhibition of inflammation |
|---|---|---|
| p-allylaminophenylacetic acid | 45 | 32 |
| ethyl p-allylaminophenylacetate | 67 | 39 |
| p-ethylaminophenylacetic acid | 81 | 23 |
| p-n-propylaminophenylacetic acid | 67 | 38 |
| p-n-butylaminophenylacetic acid | 33 | 21 |
| p-isopropylaminophenylacetic acid | 67 | 42 |
| p-benzylaminophenylacetic acid | 67 | 26 |
| p-propargylaminophenylacetic acid | 81 | 18 |
| 2-(p-allylaminophenyl)propionic acid | 50 | 50 |
| methyl 2-(p-allylaminophenyl)propionate | 50 | 35 |
| 2-(p-methylaminophenyl)propionic acid | 89 | 44 |
| 2-(p-ethylaminophenyl)propionic acid | 67 | 47 |
| 2-(p-n-propylaminophenyl)-propionic acid | 67 | 47 |
| 2-(p-n-butylaminophenyl)propionic acid | 33 | 33 |
| 2-(p-isopropylaminophenyl)propionic acid | 67 | 44 |
| 2-(p-benzylaminophenyl)propionic acid | 25 | 12 |
| 2-(p-methallylaminophenyl)propionic acid | 67 | 51 |
| 2-(p-propargylaminophenyl)propionic acid | 67 | 47 |
| methyl 2-(p-methallylaminophenyl)-propionate hydrochloride | 67 | 46 |
| ethyl p-methallylaminophenylacetate | 67 | 38 |
| p-methallylaminophenylacetic acid | 49 | 25 |
| 2-(p-allylaminophenyl)propionic acid, lithium salt | 81 | 59 |
| indometacine | 5 | 37 |

*Doses corresponding to about 1/36 of $LD_{50}$, except in the case of indometacine where the dose corresponds to about 1/10 of LD 50.

Having now described my invention what I claim as new and desire to secure by Letters Patent is:

1. Compounds selected from the group consisting of phenylacetic acid derivatives having the general formula

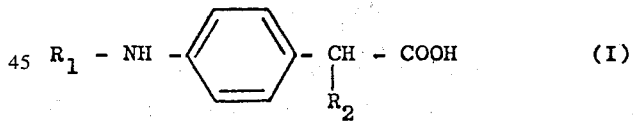

$$R_1 - NH - \langle\phantom{O}\rangle - CH - COOH \qquad (I)$$
$$\phantom{R_1 - NH - \langle\phantom{O}\rangle - }R_2$$

in which $R_1$ is selected from the group consisting of ethyl, n-propyl, isopropyl, n-butyl. benzyl, allyl, methallyl and propargyl and $R_2$ is selected from the group consisting of hydrogen and methyl, the methyl and ethyl esters thereof and their pharmaceutically acceptable salts.

2. Compound as claimed in claim 1, wherein $R_2$ is hydrogen.

3. Compound as claimed in claim 2, wherein $R_1$ is ethyl.

4. Compound as claimed in claim 2, wherein $R_1$ is n-propyl.

5. Compound as claimed in claim 2, wherein $R_1$ is n-butyl.

6. Compound as claimed in claim 2, wherein $R_1$ is isopropyl.

7. Compound as claimed in claim 2, wherein $R_1$ is benzyl.

8. Compound as claimed in claim 2, wherein $R_1$ is allyl.

9. Compound as claimed in claim 2, wherein $R_1$ is methallyl.

10. Compound as claimed in claim 2; wherein $R_1$ is propargyl.

11. Compound as claimed in claim 1, wherein $R_2$ is methyl.

12. Compound as claimed in claim 11, wherein $R_1$ is ethyl.

13. Compound as claimed in claim 11, wherein $R_1$ is n-propyl.

14. Compound as claimed in claim 11, wherein $R_1$ is n-butyl.

15. Compound as claimed in claim 11, wherein $R_1$ is isopropyl.

16. Compound as claimed in claim 11, wherein $R_1$ is benzyl.

17. Compound as claimed in claim 11, wherein $R_1$ is allyl.

18. Compound as claimed in claim 11, wherein $R_1$ is methallyl.

19. Compound as claimed in claim 11, wherein $R_1$ is propargyl.

* * * * *